United States Patent
Vacher et al.

(12)

(10) Patent No.: US 6,231,877 B1
(45) Date of Patent: May 15, 2001

(54) COSMETIC COMPOSITION EXPLOITING SYNERGISTIC RADICAL SCAVENGING EFFECTS

(75) Inventors: Anne-Marie Vacher, Le Chesnay; Marie-Claire Fritsch, Paris, both of (FR)

(73) Assignee: Lanatech Laboratoire Nature et Technique (FR)

( * ) Notice: Subject to any disclaimer, the term of this patent is extended or adjusted under 35 U.S.C. 154(b) by 0 days.

(21) Appl. No.: 09/339,950

(22) Filed: Jun. 25, 1999

(30) Foreign Application Priority Data

Jul. 3, 1998 (FR) .................................................. 98 08720

(51) Int. Cl.[7] .............................. A61K 6/00; A61K 7/00; A61K 7/06; A01N 65/00
(52) U.S. Cl. ...................... 424/401; 424/195.1; 424/70.1
(58) Field of Search .................................. 424/70.1, 401, 424/195.1

(56) References Cited

U.S. PATENT DOCUMENTS 5,958,437 * 9/1999 Zaveri .................................. 424/401

* cited by examiner

*Primary Examiner*—Thurman K. Page
*Assistant Examiner*—S. Howard
(74) *Attorney, Agent, or Firm*—William A. Drucker

(57) ABSTRACT

The composition embodying the invention comprises an extract of chrysanthellum and at least one of the following list of compounds: a plant extract which is rich in phenolic compounds, a plant extract which is rich in carotenoids, a plant oil which is rich in tocopherols, an antioxidant of natural or synthetic origin and an enzymatic system for trapping free radicals, this composition exploiting synergistic radical-scavenging between the chrysanthellum and the compounds of this list.

14 Claims, No Drawings

COSMETIC COMPOSITION EXPLOITING SYNERGISTIC RADICAL SCAVENGING EFFECTS

BACKGROUND OF THE INVENTION

1. Field of the Invention

The present invention relates to an improvement to the composition for preventing ageing of the skin, which is the subject of patent PCT/FR 97/02017, filed on Nov. 10, 1997 in the name of the Applicant.

The invention similarly applies both to natural ageing and to phenomena of accidental ageing of the skin due to the manifold attacking factors to which the skin is subjected daily, in particular solar radiation. 2. Description of the Prior Art In general, it is known that free radicals (aggressive particles possessing a free electron) are the main agents incriminated in skin damage caused, for example, either by prolonged exposure to solar radiation and thus to the ultraviolet rays included in this radiation, or even by metabolic and enzymatic reactions which take place in the body.

Radical attack initiates chain reactions which stop only when two free radicals become mutually inactivated.

Lipid peroxidation (lipoperoxidation) is a typical case of a radical-induced chain reaction.

Oxidation of the membrane lipids results in the formation of lipoperoxides, which decompose into various fragmentation products, some of which are highly aggressive.

One of the most important and most aggressive fragmentation products is an aldehyde, malondialdehyde (MDA), which exhibits formidable toxicity by transversely bridging proteins, intracellular lipids and DNA.

It thus appears that the free radicals and the cascade of chain reactions to which they give rise in the body play a very important role in the process of ageing of the skin.

With the aim of combating this radical action, the Applicant proposes a composition which uses the properties of Chrysanthellum indicum indicum, which, according to the abovementioned French patent:

has very good radical-scavenging properties, so as to obtain anti-ageing action both for natural and accidental ageing;

ensures effective protection against the reactions leading to the production of OH° radicals or radicals of oxoferryl type;

reduces the fall in the ATP content of the keratinocytes after irradiation, so as to obtain a repairing effect.

Hitherto, as many scientific publications affirm, the studies carried out on Chrysanthellum indicum revealed the clinical effects in essentially circulatory and digestive pathologies (exclusively medical field).

Only French patent No. 87/10502 proposed a cosmetic composition comprising an extract of Chrysanthellum indicum containing from 1% to 10% extract of Chrysanthellum indicum, for applications such as shampoos and hair lotions, dermal emulsions, body milks, lipsticks or even cosmetic compositions in the form of aerosols.

Besides the fact that that document does not mention the prevention of ageing of the skin, the concentrations recommended therein give products which are entirely inappropriate and even incompatible with normal cosmetic use, since, at these concentrations, emulsions for topical use exhibit, in particular:

a dark brown coloration which causes the skin to be treated and that of the fingers used to carry out the application to be dyed an intense mustard-yellow colour. The strong intensity of this dyeing is attenuated on rinsing, but leaves a dark yellow coloration after washing.

Poor stability over time: a concentration of water in the bottom of the container and considerable release of oil at the surface are observed from 24 hours onwards.

A strong odour of plant extract.

OBJECT OF THE INVENTION

A subject of the invention is thus, more particularly, a composition based on Chrysanthellum indicum in which the radical-scavenging effect is enhanced, without needing to increase the content of Chrysanthellum indicum, which must remain at a sufficiently low level in order to avoid the drawbacks mentioned above.

SUMMARY OF THE INVENTION

To this end, the invention proposes to use synergistic radical-scavenging effects, i.e. the effects obtained by combining one or more molecules with the Chrysanthellum indicum.

Now, it is known that such a combination can give:

a) either weaker activity than addition of the activity of each of the products, on account of an antagonistic effect (one product reducing the activity of the other) or of a saturation effect (impossibility of exceeding the maximum effect reached) or even a harmful effect (predominant antagonistic effect);

b) or an activity which is equal to the sum of the activities of each of the products tested separately;

c) or to higher activity than the sum of the activities of the products tested separately (synergistic effect).

d)

DESCRIPTION OF THE PREFERRED EMBODIMENTS

In practice, as much as it is conceivable that there may be an activity threshold which cannot be exceeded, it is implausible to hope to obtain additional effects, even partial effects. The demonstration of synergistic effects, for its part, is very rare.

As regards Chrysanthellum indicum, no synergistic radical-scavenging effect involving it was known hitherto and there was no indication to predict that it would be possible to demonstrate a synergistic effect between Chrysanthellum indicum and other molecules, or even that this type of combination would allow the already excellent performance levels to be improved.

Now, the studies conducted by the Applicant have revealed such a synergistic effect.

The aims of these studies, carried out in vitro, were:
on the one hand, to measure the effects of four compounds:

extract of Chrysanthellum indicum,
  extract of green tea,
  extract of Ginkgo biloba,
  DL-α-tocopheryl acetate, with respect to the peroxidation of linoleic acid by OH° and peroxyferryl radicals,
on the other hand, to investigate any potentiation between Chrysanthellum indicum and one of the other compounds.

To this end, each of the compounds was subjected to the lipid peroxidation initiation treatment below:

Peroxidation of a linoleic acid emulsion was induced by radicals of the type: hydroxyl OH° and oxyferryl. Linoleic acid (10 mg) was emulsified with 0.2% of 3-[(3-cholamidopropyl)dimethylammonio]-1-propane-sulphonate (CHAPS), in a pH 7.3 phosphate buffer (50 ml).

The OH° radicals are produced using a source of gamma irradiation. Under these conditions, the irradiation is carried out at 20° C. for 18 hours (source$^{131}$ Cs, total dose: 180 grays/18,000 rads).

The oxyferryl radicals are generated by adding 10 μl of haemoglobin to a linoleic acid emulsion (2 ml) for 3 hours (incubation at 40° C.).

These tests were carried out in 10 ml leakproof bottles in the presence or absence of two control antioxidants. Each test was performed in triplicate.

At the end of the reaction under the various conditions mentioned above, the lipid peroxidation is measured by means of determining the pentane (nmol) resulting from the decomposition of the lipid peroxides. The emission of pentane is directly proportional to the peroxidation. The pentane is measured by gas chromatography: 0.1 ml of the atmosphere from the flask in which the reaction took place are injected using a Hamilton syringe into a Varian 3600 type chromatograph.

This chromatograph is equipped with a GF molecular sieve alltech column (length: 1m; ID: ⅛") at 140° C., the carrier gas used being nitrogen (40 ml/min). The method is calibrated using pure pentane.

The results of these measurements are given in Tables I and II below.

TABLE I

"Anti-oxyferryl" effect (release of pentane, in nmol)

| Concentration (μg/ml) | Chrysanthellum | Green tea | Ginkgo biloba | Tocopherol | Concentration (μM) |
|---|---|---|---|---|---|
| 0.00 | 100.00 | 100.00 | 100.00 | 100.00 | 0.00 |
| 0.15 | 101.39 | 110.83 | 122.77 | 93.02 | 1.00 |
| 1.50 | 97.70 | 93.85 | 104.63 | 82.17 | 2.50 |
| 15.00 | 82.77 | 87.61 | 93.00 | 72.33 | 5.00 |
| 150.00 | 40.77 | 44.93 | 65.73 | 57.07 | 7.50 |
| 300.00 | 11.17 | 24.33 | 35.47 | 36.80 | 10.00 |

TABLE II

"Anti-hydroxyl" effect (release of pentane)

| Concentration (μg/ml) | Chrysanthellum | Green tea | Ginkgo biloba | Tocopherol | Concentration (μM) |
|---|---|---|---|---|---|
| 0.00 | 100.00 | 100.00 | 100.00 | 100.00 | 0.00 |
| 0.15 | 101.41 | 108.43 | 115.43 | 119.67 | 1.00 |
| 1.50 | 86.67 | 97.30 | 100.37 | 66.76 | 2.50 |
| 15.00 | 30.50 | 36.93 | 98.87 | 13.70 | 5.00 |
| 150.00 | 12.73 | 23.03 | 53.87 | 7.67 | 7.50 |
| 300.00 | 7.97 | 12.10 | 29.90 | 5.59 | 10.00 |

As emerges from these results, the three plant extracts inhibit the release of pentane induced by the oxyferryl radical.

The extract of Chrysanthellum indicum proves to be the best inhibitor of the peroxidation induced by the oxyferryl radical. The extract of green tea has an effect similar to that of Chrysanthellum indicum, whereas the extract of Ginkgo appears to be markedly less protective.

A protective effect of the three extracts is also observed in the case of the production of pentane induced by the hydroxyl radical. This protection is more pronounced than that observed for the induction induced by the oxyferryl radical.

Tocopherol also exerts a protective effect. Its effect is markedly more pronounced on the peroxidation induced by the OH° radical than on that induced by the peroxyferryl radical. This dissociation of the effects appears to be greater than that recorded with the three plant extracts.

The investigation of a synergistic effect between the extract of Chrysanthellum indicum and the extract of green tea, the extract of Gingko biloba or tocopherol led to the above studies being repeated, but with compositions each including an extract of Chrysanthellum indicum and one of these compounds.

The results of these measurements are given in Tables III and IV below.

TABLE III

"Anti-oxyferryl" effect of *Chrysanthellum indicum* in combination (release of pentane, in nmol)

| Concentration (μg/ml) of *Chrysanthellum indicum* | ⊕ green tea 1.5 μg/ml | ⊕ green tea 15 μg/ml | ⊕ Ginkgo 15 μg/ml | ⊕ Gingko 150 μg/ml | ⊕ Tocopherol 5 μM | ⊕ Tocopherol 7.5 μM |
|---|---|---|---|---|---|---|
| 0.00 | 100.00 | 100.00 | 100.00 | 100.00 | 100.00 | 100.00 |
| 0.15 | 92.50 | 89.60 | 102.81 | 79.00 | 101.53 | 94.67 |
| 1.50 | 84.77 | 58.50 | 95.77 | 71.90 | 92.62 | 85.03 |

TABLE III-continued

"Anti-oxyferryl" effect of *Chrysanthellum indicum* in combination (release of pentane, in nmol)

| Concentration (µg/ml) of *Chrysanthellum indicum* | ⊕ green tea 1.5 µg/ml | ⊕ green tea 15 µg/ml | ⊕ Ginkgo 15 µg/ml | ⊕ Gingko 150 µg/ml | ⊕ Tocopherol 5 µM | ⊕ Tocopherol 7.5 µM |
|---|---|---|---|---|---|---|
| 15.00 | 78.03 | 55.47 | 80.80 | 61.00 | 81.28 | 76.00 |
| 150.00 | 41.63 | 31.60 | 42.67 | 34.10 | 41.87 | 43.99 |
| 300.00 | 10.97 | 6.17 | 10.80 | 8.57 | 11.90 | 9.33 |

TABLE IV

"Anti-hydroxyl" effect of *Chrysanthellum indicum* in combination (release of pentane, in nmol)

| Concentration (µg/ml) of *Chrysanthellum indicum* | ⊕ green tea 1.5 µg/ml | ⊕ green tea 15 µg/ml | ⊕ Ginkgo 15 µg/ml | ⊕ Gingko 150 µg/ml | ⊕ Tocopherol 5 µM | ⊕ Tocopherol 7.5 µM |
|---|---|---|---|---|---|---|
| 0.00 | 100.00 | 100.00 | 100.00 | 100.00 | 100.00 | 100.00 |
| 0.15 | 96.53 | 85.50 | 101.80 | 87.07 | 96.50 | 91.57 |
| 1.50 | 78.53 | 69.80 | 86.13 | 72.30 | 79.64 | 76.67 |
| 15.00 | 26.43 | 22.57 | 28.07 | 30.40 | 28.33 | 19.54 |
| 150.00 | 12.15 | 8.28 | 14.08 | 14.02 | 12.80 | 8.83 |
| 300.00 | 4.34 | 4.76 | 6.43 | 6.38 | 6.37 | 5.00 |

Analysis of the results is carried out from Tables V and VI below, for which the following rules are applied:

Protection=(100−release of pentane) Total protection= 100

No protection=0

Synergistic effect if protection (A+B)>protection A+protection B

Total additive effect if protection (A+B)=protection A+protection B

Partial additive effect if protection (A+B)<protection A+protection B with protection (A+B)>protection A and protection (A+B)>protection B

TABLE V

"Anti-oxyferryl" effect

| A | B | Protection A + protection B | Protection (A + B) observed | Gain in protection | Type of effect |
|---|---|---|---|---|---|
| Chrysanthellum 0.15 µg/ml | Green tea 1.5 µg/ml | 4.76 | 7.50 | +58% relative to A + B | Strong synergistic effect |
| Chrysanthellum 1.50 µg/ml | Green tea 1.5 µg/ml | 8.45 | 15.23 | +80% relative to A + B | Very strong synergistic effect |
| Chrysanthellum 15.00 µg/ml | Green tea 1.5 µg/ml | 23.38 | 21.97 | (A + B) > A and (A + B) > B | Partial additive effect |
| Chrysanthellum 1.50 µg/ml | Green tea 15 µg/ml | 14.69 | 41.50 | +182% relative to A + B | Very strong synergistic effect |
| Chrysanthellum 15.00 µg/ml | Green tea 15 µg/ml | 29.62 | 44.53 | +50% relative to A + B | Strong synergistic effect |
| Chrysanthellum 150. µg/ml | Green tea 15 µg/ml | 71.62 | 68.40 | (A + B) > A and (A + B) > B | Partial additive effect |
| Chrysanthellum 300.00 µg/ml | Green tea 15 µg/ml | >100 | 93.83 | (A + B) > A and (A + B) > B | Partial additive effect |

TABLE V-continued

"Anti-oxyferryl" effect

| A | B | Protection A + protection B | Protection (A + B) observed | Gain in protection | Type of effect |
|---|---|---|---|---|---|
| Chrysathellum 15.00 μg/ml | Ginkgo biloba 15 μg/ml | 24.23 | 19.20 | (A + B) > A and (A + B) > B | Partial additive effect |
| Chrysanthellum 15.00 μg/ml | Ginkgo biloba 150 μg/ml | 51.50 | 39.00 | (A + B) > A and (A + B) > B | Partial additive effect |
| Chrysanthellum 150.00 μg/ml | Ginkgo biloba 150 μg/ml | 93.50 | 65.90 | (A + B) > A and (A + B) > B | Partial additive effect |
| Chrysanthellum 300.00 μg/ml | Ginkgo biloba 150 μg/ml | >100 | 91.43 | (A + B) > A and (A + B) > B | Partial additive effect |
| Chrysanthellum 300.00 μg/ml | Tocopherol 7.5 μM | >100 | 90.67 | (A + B) > A and (A + B) > B | Partial additive effect |

TABLE VI

"Anti-hydroxyl" effect

| A | B | Protection A + protection B | Protection (A + B) observed | Gain in protection | Type of effect |
|---|---|---|---|---|---|
| Chrysanthellum 0.15 μg/ml | Green tea 1.5 μg/ml | 1.29 | 3.47 | +169% relative to A + B | Very strong synergistic effect |
| Chrysanthellum 1.50 μg/ml | Green tea 1.5 μg/ml | 16.03 | 21.47 | +34% relative to A + B | Good synergistic effect |
| Chrysanthellum 15.00 μg/ml | Green tea 1.5 μg/ml | 72.20 | 73.57 | +2% relative to A + B | Total additive effect |
| Chrysanthellum 300.00 μg/ml | Green tea 1.5 μg/ml | 94.73 | 95.66 | +1% relative to A + B | Total additive effect |
| Chrysanthellum 15.00 μg/ml | Green tea 15 μg/ml | >100 | 77.43 | (A + B) > A and (A + B) > B | Partial additive effect |
| Chrysanthellum 150.00 μg/ml | Green tea 15 μg/ml | >100 | 91.72 | (A + B) > A and (A + B) > B | Partial additive effect |
| Chrysanthellum 300.00 μg/ml | Green tea 15 μg/ml | >100 | 95.24 | (A + B) > A and (A + B) > B | Partial additive effect |
| Chrysathellum 15.00 μg/ml | Ginkgo biloba 15 μg/ml | 70.63 | 71.93 | +2% relative to A + B | Total additive effect |
| Chrysanthellum 300.00 μg/ml | Ginkgo biloba 15 μg/ml | 93.16 | 93.57 | +0.5% relative to A + B | Total additive effect |
| Chrysanthellum 300.00 μg/ml | Ginkgo biloba 150 μg/ml | >100 | 93.62 | (A + B) > A and (A + B) > B | Partial additive effect |
| Chrysanthellum 300.00 μg/ml | Tocopherol 5 μM | >100 | 93.63 | (A + B) > A and (A + B) > B | Partial additive effect |
| Chrysanthellum 300.00 μg/ml | Tocopherol 7.5 μM | >100 | 95 | (A + B) > A and (A + B) > B | Partial additive effect |

The analysis of the results of this study performed in vitro shows that, against all expectations, the excellent radical-scavenging activity of Chrysanthellum indicum (demonstrated in the past) can be further enhanced by addition of other molecules or plant extracts known for their antioxidant and/or radical-scavenging properties. In the various cases studied (an exhaustive study of all of the possible combinations is difficult to carry out), very good results were obtained, irrespective of the model of production of free radicals used.

Two types of positive effect were observed:

Synergistic effects (gain in protection observed ranging from +34% to +182% relative to an additive effect). This synergistic effect is observed in several cases (various concentrations of Chrysanthellum indicum and of combined extracts) and is particularly outstanding in the case of a combination with green tea. Such synergistic effects are noteworthy.

Total or partial additive effect. Given the very good results obtained with Chrysanthellum indicum alone, and given the existence of a threshold of maximum efficacy, it was not obvious that additive effects could be obtained. Total or partial additive effects were, however, obtained in various Chrysanthellum indicum/ other radical-scavenging substance combinations, which, here also, is quite noteworthy.

The discovery of these synergistic radical-scavenging effects is particularly advantageous especially in the field of cosmetic or dermocosmetic care intended to:

prevent ageing of the skin and repair the damage caused by radical attack on the skin, protect and repair hair exposed to damage caused by ultraviolet rays and other environmental attacking factors which generate an excess of free radicals.

Given these results, the invention proposes a radical-scavenging cosmetic composition which can be used to care for the skin and the hair, and comprising, on the one hand, an extract of Chrysanthellum indicum, and at least one of the following compounds:

a plant extract which is rich in phenolic compounds, a plant extract which is rich in carotenoids, a plant oil which is rich in tocopherols, an antioxidant of natural or synthetic origin, an enzymatic system for trapping free radicals.

The Chrysanthellum indicum may consist of Chrysanthellum indicum, Chrysanthellum americanum or Chrysanthellum procumbens.

The phenolic compounds may comprise polyphenols, in particular flavonoids, or phenolic acids.

The plant extracts may be extracts of green tea (Camelia sinensis), of Ginkgo biloba, of camomile or of brown algae of the genus Ascophyllum. They may also consist of plant extracts of the Labiatae family, which are known for their antioxidant properties (rosemary, sage, thyme).

The plant oils which are rich in tocopherols may consist of wheatgerm oil, soybean oil or buckwheat oil.

The antioxidant of natural or synthetic origin may comprise caffeic acid, gallic acid, ascorbic acid, ascorbyl palmitate, cinnamic acid, nordihydroguiaretic acid, uric acid, hesperetin, heperidin, lecithin, quercetin, rosmarinic acid, rosmanol, carnosol, carnosic acid, vitamin E (tocopherols), butylated hydroxyanisole, butylated hydroxytoluene, ethoxyquin, ferulic acid, hydroquinone, tert-butylhydroquinone, para-hydroxyanisole, propyl gallate or other gallic acid derivatives, tocopheryl acetate, tocopheryl linoleate and/or other tocopherol esters.

The enzymatic systems may, for their part, comprise a superoxide dismutase.

The extract of Chrysanthellum indicum and the plant extracts possibly combined may be dry extracts, water-soluble fluid extracts, oily extracts or dry extracts in solution (in water, glycols or glycerol). These plant extracts or these purified molecules of natural or synthetic origin may also be encapsulated.

Needless to say, the compositions according to the invention may be in the form of simple or multiple emulsions (water/oil or oil/water creams or milks, triple emulsions, microemulsions or liquid-crystal emulsions), aqueous or oily gels, aqueous, oily, aqueous-alcoholic or two-phase lotions, sticks, powders or any vectorized system ("controlled-release" system or "modulated-release" systems). They will be used topically.

Examples of formulation of the composition according to the invention will be described below, as non-limiting examples:

| Radical-scavenging repairing shampoo | |
|---|---|
| Water | QS 100% |
| Cocamidopropyl betaine | 15 to 20% |
| Alkyl ether sulphates | 10 to 15% |
| Caprylyl/capryl glucoside | 2 to 10% |
| Cocamide DEA | 2 to 4% |
| Glycerol | 1 to 5% |
| PEG-120 Methyl Glucose Dioleate | 1 to 5% |
| Fragrance | 0.2 to 1% |
| Preserving agent | 0.05 to 0.8% |
| EDTA | 0.05 to 0.1% |
| *Ginkgo biloba* (dry extract) | 0.0001 to 1% |
| *Chrysanthellum indicum* (dry extract) | 0.0001 to 0.1% |

| Hair mask | |
|---|---|
| Water | QS 100% |
| PEG-6 Stearate & Ceteth-20 & glyceryl stearate & Steareth-20 | 5 to 10% |
| Cetyl alcohol | 2 to 5% |
| Quaternium-80 | 1 to 5% |
| Karite butter | 1 to 5% |
| Mineral oils and emollient esters | 1 to 5% |
| Glycerol | 1 to 5% |
| Dimethicone copolyol | 1 to 3% |
| Fragrance | 0.1 to 1% |
| Preserving agent | 0.1 to 0.7% |
| Carbomer | 0.05 to 0.5% |
| Triethanolamine | 0.05 to 0.5% |
| *Camelia sinensis* = Green tea (dry extract) | 0.0001 to 1% |
| *Chrysanthellum indicum* (dry extract) | 0.0001 to 0.1% |

| Protective day cream | |
|---|---|
| Water | QS 100% |
| Emollient esters | 10 to 15% |
| Glyceryl stearate & PEG-100 stearate | 4 to 6% |
| Butylene glycol | 2 to 5% |
| Wheatgerm oil | 2 to 5% |
| Cetyl alcohol | 1 to 5% |
| Dimethicone | 1 to 4% |
| Polymethyl methacrylate | 0.5 to 2% |
| Fragrance | 0.3 to 1% |
| Preserving agent | 0.1 to 0.8% |
| Carbomer | 0.05 to 0.5% |
| Triethanolamine | 0.05 to 0.5% |
| Butylated hydroxytoluene | 0.05 to 0.1% |
| *Chrysanthellum indicum* (dry extract) | 0.0001 to 0.1% |

What is claimed is:

1. Cosmetic composition for preventing ageing of the skin and the hair this composition exploiting synergistic radical-scavenging effects and containing an extract of Chrysanthellum indicum, characterized in that it also comprises at least one of the following compounds:

a plant extract which is rich in phenolic compounds, a plant extract which is rich in carotenoids, a plant oil which is rich in tocopherols, an antioxidant of natural or synthetic origin, an enzymatic system for trapping free radicals.

2. Composition according to claim 1, wherein the chrysanthellum is Chrysanthellum indicum, Chrysanthellum americanum or Chrysanthellum procumbens.

3. Composition according to claim 1, wherein the concentration of Chrysanthellum indicum comprises from 0.0001% to 0.1% by weight of equivalents of dry extracts.

4. Composition according to claim 1, wherein the extract of Chrysanthellum indicum and/or the plant extracts combined are dry extracts, water-soluble fluid extracts, oily extracts or dry extracts in solution.

5. Composition according to claim 1, wherein the extract of Chrysanthellum indicum and/or the plant extracts combined and/or the antioxidant or purified enzymatic molecules of natural or synthetic origin are encapsulated.

6. Composition according to claim 1, wherein the plant extract which is rich in phenolic compounds comprises a polyphenol such as a flavonoid and/or a phenolic acid.

7. Composition according to claim 6, wherein the plant extract comprises extracts of green tea, of Ginkgo biloba, of camomile and/or of brown alga of the genus ascophyllum.

8. Composition according to claim 6, wherein the plant extract consists of an extract of a plant from the Labiatae family, such as rosemary, sage or thyme.

9. Composition according to claim 1, wherein the plant oil which is rich in tocopherols is extracted from wheatgerm, from soybean and/or from buckwheat.

10. Composition according to claim 1, wherein the antioxidant of natural or synthetic origin comprises caffeic acid, gallic acid, ascorbic acid, ascorbyl palmitate, cinnamic acid, nordihydroguiaretic acid, uric acid, hesperetin, heperidin, lecithin, quercetin, rosmarinic acid, rosmanol, carnosol, carnosic acid, vitamin E (tocopherols), butylated hydroxyanisole, butylated hydroxytoluene, ethoxyquin, ferulic acid, hydroquinone, tert-butylhydroquinone, para-hydroxyanisole, propyl gallate or other gallic acid derivatives, tocopherols, tocopheryl acetate, tocopheryl linoleate and/or other tocopherol esters.

11. Composition according to claim 1, wherein the enzymatic systems comprise a superoxide dismutase.

12. Radical-scavenging repairing shampoo, comprising:

| | |
|---|---|
| Water | QS 100% |
| Cocamidopropyl betaine | 15 to 20% |
| Alkyl ether sulphates | 10 to 15% |
| Caprylyl/capryl glucoside | 2 to 10% |
| Cocamide DEA | 2 to 4% |
| Glycerol | 1 to 5% |
| PEG-120 methyl glucose dioleate | 1 to 5% |
| Fragrance | 0.2 to 1% |
| Preserving agent | 0.05 to 0.8% |
| EDTA | 0.05 to 0.1% |
| *Ginkgo biloba* (dry extract) | 0.0001 to 1% |
| *Chrysanthellum indicum* (dry extract) | 0.0001 to 0.1%. |

13. Hair mask, comprising:

| | |
|---|---|
| Water | QS 100% |
| PEG-6 Stearate & Ceteth-20 & glyceryl stearate & Steareth-20 | 5 to 10% |
| Cetyl alcohol | 2 to 5% |
| Quaternium-80 | 1 to 5% |
| Karite butter | 1 to 5% |
| Mineral oils and emollient esters | 1 to 5% |
| Glycerol | 1 to 5% |
| Dimethicone copolyol | 1 to 3% |
| Fragrance | 0.1 to 1% |
| Preserving agent | 0.1 to 0.7% |
| Carbomer | 0.05 to 0.5% |
| Triethanolamine | 0.05 to 0.5% |
| *Camelia sinensis* = Green tea (dry extract) | 0.0001 to 1% |
| *Chrysanthellum indicum* (dry extract) | 0.0001 to 0.1%. |

14. Protective day cream, comprising:

| | |
|---|---|
| Water | QS 100% |
| Emollient esters | 10 to 15% |
| Glyceryl stearate & PEG-100 stearate | 4 to 6% |
| Butylene glycol | 2 to 5% |
| Wheatgerm oil | 2 to 5% |
| Cetyl alcohol | 1 to 5% |
| Dimethicone | 1 to 4% |
| Polymethyl methacrylate | 0.5 to 2% |
| Fragrance | 0.3 to 1% |
| Preserving agent | 0.1 to 0.8% |
| Carbomer | 0.05 to 0.5% |
| Triethanolamine | 0.05 to 0.5% |
| Butylated hydroxytoluene | 0.05 to 0.1% |
| *Chrysanthellum indicum* (dry extract) | 0.0001 to 0.1%. |

* * * * *